United States Patent
Zabudkin et al.

(10) Patent No.: US 10,308,665 B2
(45) Date of Patent: Jun. 4, 2019

(54) METHOD FOR THE SYNTHESIS OF RAPAMYCIN DERIVATIVES

(71) Applicant: Synbias Pharma AG, Schaffhausen (CH)

(72) Inventors: Oleksandr Zabudkin, Gerusbach (DE); Christian Schickaneder, Lauf an der Pegnitz (DE); Iaroslav Matviienko, Mannheim (DE); Volodymyr Sypchenko, Mannheim (DE)

(73) Assignee: Synbias Pharma AG, Schaffhausen (CH)

( * ) Notice: Subject to any disclaimer, the term of this patent is extended or adjusted under 35 U.S.C. 154(b) by 0 days.

(21) Appl. No.: 15/737,861

(22) PCT Filed: Jun. 22, 2016

(86) PCT No.: PCT/EP2016/064389
§ 371 (c)(1),
(2) Date: Dec. 19, 2017

(87) PCT Pub. No.: WO2016/207205
PCT Pub. Date: Dec. 29, 2016

(65) Prior Publication Data
US 2019/0010168 A1   Jan. 10, 2019

(30) Foreign Application Priority Data

Jun. 23, 2015 (EP) .................... 15173283

(51) Int. Cl.
*C07D 211/06* (2006.01)
*C07D 295/00* (2006.01)
*C07D 498/16* (2006.01)
*C07D 498/18* (2006.01)

(52) U.S. Cl.
CPC ......... *C07D 498/16* (2013.01); *C07D 498/18* (2013.01)

(58) Field of Classification Search
CPC ........................ C07D 211/06; C07D 295/00
USPC .................................... 546/89, 184
See application file for complete search history.

(56) References Cited

FOREIGN PATENT DOCUMENTS

| CN | 102127092 A | 7/2011 |
|---|---|---|
| CN | 102268015 A | 12/2011 |
| CN | 102786534 A | 11/2012 |
| CN | 103848849 A | 6/2014 |
| CN | 104478898 A | 4/2015 |
| WO | 2007/135397 A1 | 11/2007 |
| WO | 2012/103960 A1 | 8/2012 |
| WO | 2014/082286 A1 | 6/2014 |

OTHER PUBLICATIONS

Levin et al., Synthesis of C6F5-Substituted Aminoethanols via Acetate Ion Mediated C6F5-Group Transfer Reaction. Synthesis. 2006;3:489-495.
International Search Report and Written Opinion for Application No. PCT/EP2016/064389, dated Aug. 2, 2016. 10 pages.
Fei et al., Review of Synthetic Routes of Everolimus. World Notes on Antibiotics. 2014;35(1):12-15.

*Primary Examiner* — Niloofar Rahmani
(74) *Attorney, Agent, or Firm* — McCarter & English, LLP; Steven G. Davis; Wei Song

(57) ABSTRACT

The present invention relates to a method for the production of a rapamycin derivative of formula (I), the method comprising the preparation of a 2-(tri-substituted silyl)oxyethyl triflate by reacting ethylene oxide and a tri-substituted silyl triflate, reaction of the resulting 2-(tri-substituted silyl)oxyethyl triflate with rapamycin in the presence of a molar excess of organic base, and deprotection to obtain the rapamycin derivative of compound (I).

14 Claims, 4 Drawing Sheets

METHOD FOR THE SYNTHESIS OF RAPAMYCIN DERIVATIVES

CROSS-REFERENCE TO RELATED APPLICATIONS

This application is a U.S. national stage filing, under 35 U.S.C. § 371(c) of International Application No. PCT/EP2016/064389, filed on Jun. 22, 2016, which claims priority to European Patent Application No. 15143283.1, filed on Jun. 23, 2015. The entire contents of each of the aforementioned applications are incorporated herein by reference.

FIELD OF THE INVENTION

The present invention is directed to a method for the production of rapamycin derivatives, and particularly of everolimus, in high yield and without significant formation of undesired by-products.

BACKGROUND OF THE INVENTION

Everolimus (40-O-(2-hydroxy)ethyl-rapamycin) (FIG. 1) is a synthetic derivative of sirolimus (rapamycin) that was originally isolated from *Streptomyces hydroscopicus*. Everolimus belongs to the class of mTOR (i.e., mammalian target of rapamycin) inhibitors and is primarily used as an immunosuppressant to prevent rejection of organ transplants and for treatment of several types of cancer including gastric cancer, renal cancer, and lymphomas.

Known methods for the synthesis of everolimus are based on alkylation of the C40-hydroxyl group of rapamycin with protected 2-hydroxyethyl fluoroalkylsulfonate 1 and subsequent removal of the protecting group from the resulting compound 2 in order to obtain everolimus (FIG. 2). The most commonly used alkylation reagent in this reaction scheme is 2-((t-butyl-dimethylsilyl)oxy)ethyl trifluoromethanesulfonate (1a in FIG. 3). Compound 1a is usually obtained by means of a rather complex two-step synthesis scheme starting from ethylene glycol (FIG. 3) Due to its high instability it has to be used immediately after preparation.

The pharmacological activity of everolimus as well as a method for its manufacture was initially described in WO 94/09010 A1. Here, synthesis is accomplished by reacting rapamicyn with 4 equivalents of 2-((t-butyldimethylsilyl) oxy)ethyl trifluoromethanesulfonate in toluene at 60° C. using 2,6-lutidine as a base in order to obtain 40-O-[2-(t-butyldimethylsilyl) oxy]ethyl-rapamycin. The product is purified by chromatography and deprotected using 1N HCl in methanol. The resulting crude everolimus is then again purified by chromatography. However, the overall yield of final product, as described in WO 2012/103959 A1, is only at about 17%.

The use of a t-butyldiphenylsilyl protective group was suggested by Moenius and coworkers (Moenius, T. et al. (2000) *J. Labelled Cpd. Radiopharm.* 43, 113-120 (2000)) with regard to the synthesis of tritiated everolimus. The process employs 2-(t-butyldiphenylsilyl)oxyethyl triflate in a mixture of toluene-dimethoxyethane at 50° C. using N,N-diisopropylethylamine as a base. However, the overall yield of everolimus obtained after subsequent deprotection was also very low.

WO 2012/066502 A1 discloses the synthesis of everolimus by reacting rapamicyn with an excess of 4-8 equivalents of 2-(t-butyldimethylsilyl)oxyethyl triflate, using dichloromethane, ethyl acetate or toluene as a solvent and 2,6-lutidine as a base, followed by deprotection of the obtained t-butyldimethylsilyl-everolimus derivative. An overall yield of final product of about 45% was obtained by performing the reaction in dichloromethane and using 8 equivalents of alkylator.

The method disclosed in WO 2012/103959 A1 relates to the alkylation of rapamycin with the more stable 2-(t-hexyldimethylsilyl)oxyethyl triflate. The reaction is carried out at 70° C. with 4 equivalents of 2-(t-hexyldimethylsilyl) oxyethyl triflate in a mixture of toluene-dimethoxyethane and using N,N-diisopropylethylamine as a base. Further deprotection of the silyl group with 1N HCl in methanol results in the formation of everolimus in slightly improved overall yield (about 52%) as compared to previous methods.

However, the method of WO 2012/103959 A1 is hampered by the complicated preparation of the starting 2-(t-hexyldimethylsilyl)oxyethyl triflate. It requires purification of the product of the first reaction step, 2-((2,3-dimethylbut-2-yl)dimethylsilyloxy) ethanol, by fractional vacuum distillation, performing the second reaction step at low temperatures (−30° C.), and the requirement of an additional purification of the crude 2-(t-hexyldimethylsilyl)oxyethyl triflate. Furthermore, the method has to be performed at high temperature (70° C., cf. above), which greatly increases the probability of undesirable side reactions and of impurities being present in the crude product. Hence, chromatography purification of protected everolimus derivative is required as additional step before the purified product can be subjected to the deprotection step.

WO 2014/203185 A1 discloses the use of sterically hindered amines as bases in the synthesis of everolimus comprising reacting rapamicyn with a compound 1 (cf. FIG. 2) and removal of the protection group to obtain everolimus. The use of amines, such as N,N-diisopropylpentane-3-amine, diisopropylnonane-5-amine and N,N-diisobutyl-2,4-dimethyl-pentan-3-amine, as a base during the alkylation of rapamycin increases the stability of the alkylator 1, which results in an improved yield of everolimus. An overall yield of crude everolimus of about 67% was obtained when performing the reaction in toluene at 40° C. and using 2.5 equivalents of 2-(t-butyldiphenylsilyl)oxyethyl triflate and N,N-diisopropylpentane-3-amine as bases. However, the starting material 2-((t-butyldiphenylsilyl)oxy)ethanol that is to be employed for the preparation of the triflate compound as well as any of the above mentioned sterically hindered amines are not commercially available and difficult to prepare, which is a major drawback of this process.

Hence, there is still an ongoing need for improved methods for the synthesis of everolimus that overcome the limitations of the established synthesis routes.

In particular, there is a need for a less laborious and cost-efficient method for the preparation of 2-(tri-substituted silyl)oxyethyl triflate, thus also improving the overall yield of the synthesis of everolimus, starting from rapamycin, while minimizing the formation of undesired by-products.

Accordingly, it is an object of the present invention to provide an improved method for the synthesis of everolimus.

SUMMARY OF THE INVENTION

In one aspect, the present invention relates to a method for the production of a rapamycin derivative of formula (I), comprising:

Formula (I)

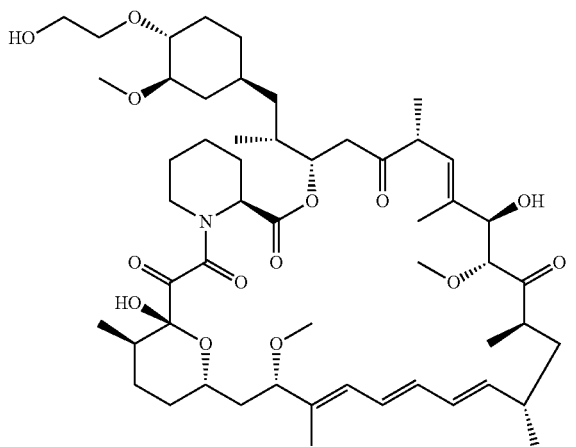

(a) preparing a 2-(tri-substituted silyl)oxyethyl triflate of formula 4 by reacting ethylene oxide and a tri-substituted silyl triflate of formula 3

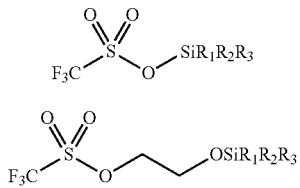

wherein $R_1$, $R_2$, and $R_3$ are independently selected from the group consisting of $C_1$-$C_{12}$ alkyl and $C_1$-$C_{12}$ aryl;

(b) reacting the 2-(tri-substituted silyl)oxyethyl triflate of formula 4 obtained in step (a) with rapamycin in the presence of a molar excess of organic base to obtain a protected rapamycin derivative of formula 5; and

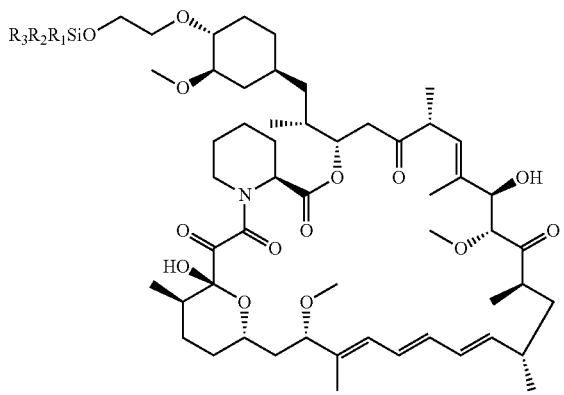

(c) deprotecting the protected rapamycin derivative of formula 5 to obtain the rapamycin derivative if formula (I). Particularly, the rapamycin derivative of formula (I) is everolimus.

In particular embodiments, $R_1$, $R_2$, and $R_3$ are independently selected from the group consisting of $C_1$-$C_6$ alkyl and $C_6$-$C_{12}$ aryl. In preferred embodiments, $R_1$, $R_2$, and $R_3$ each are isopropyl; or $R_1$ and $R_2$ each are methyl and R3 is t-butyl; or $R_1$ and $R_2$ each are phenyl and R3 is t-butyl; or $R_1$ and $R_2$ each are methyl and R3 is t-hexyl.

In further preferred embodiments, method step (a) is performed at a reaction temperature of 15° C.-45° C. in an organic solvent. Particularly preferably, the organic solvent is toluene.

In other particular embodiments, the ethylene oxide is used in an amount of 1.1-1.2 molar equivalents of the amount of tri-substituted silyl triflate of formula 3.

In other particular embodiments, the 2-(tri-substituted silyl)oxyethyl triflate of formula 4 obtained in step (a) is used without further purification.

In further preferred embodiments, method step (b) is performed at a reaction temperature of 40° C.-55° C. in an organic solvent. Particularly preferably, the organic solvent is a mixture of 85-95% (v/v) toluene and 5-15% (v/v) dimethoxyethane.

In further particular embodiments, the 2-(tri-substituted silyl)oxyethyl triflate of formula 4 is used in an amount of 4-12 molar equivalents of the amount of rapamycin.

In particularly preferred embodiments, method step (b) is performed with a molar excess of N,N-diisopropylethylamine as organic base.

In yet other particular embodiments, the protected rapamycin derivative of formula 5 obtained in step (b) is used without further purification.

In further preferred embodiments, deprotection is accomplished by reacting the protected rapamycin derivative of formula 5 with an agent selected from the group consisting of hydrochloric acid, acetic acid, tetra-n-butylammonium fluoride, and pyridine hydrofluoride.

In other particular embodiments, the method further comprises purifying the rapamycin derivative of formula (I) obtained in step (c).

DETAILED DESCRIPTION OF THE INVENTION

Figure 1:
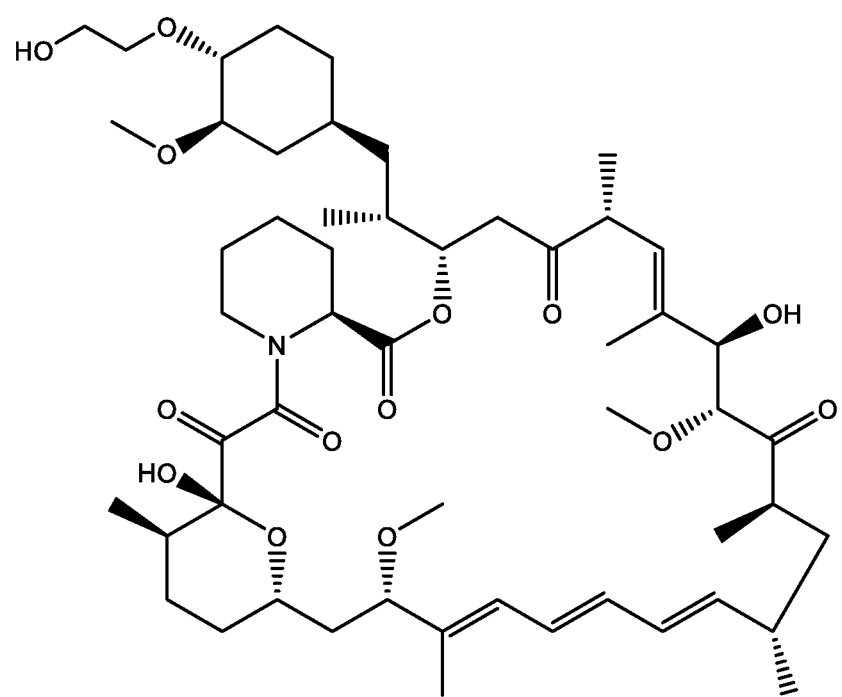
FIG. 1 illustrates the chemical structure of 40-O-(2-hydroxy)ethyl-rapamycin (i.e., everolimus).
Figure 2:
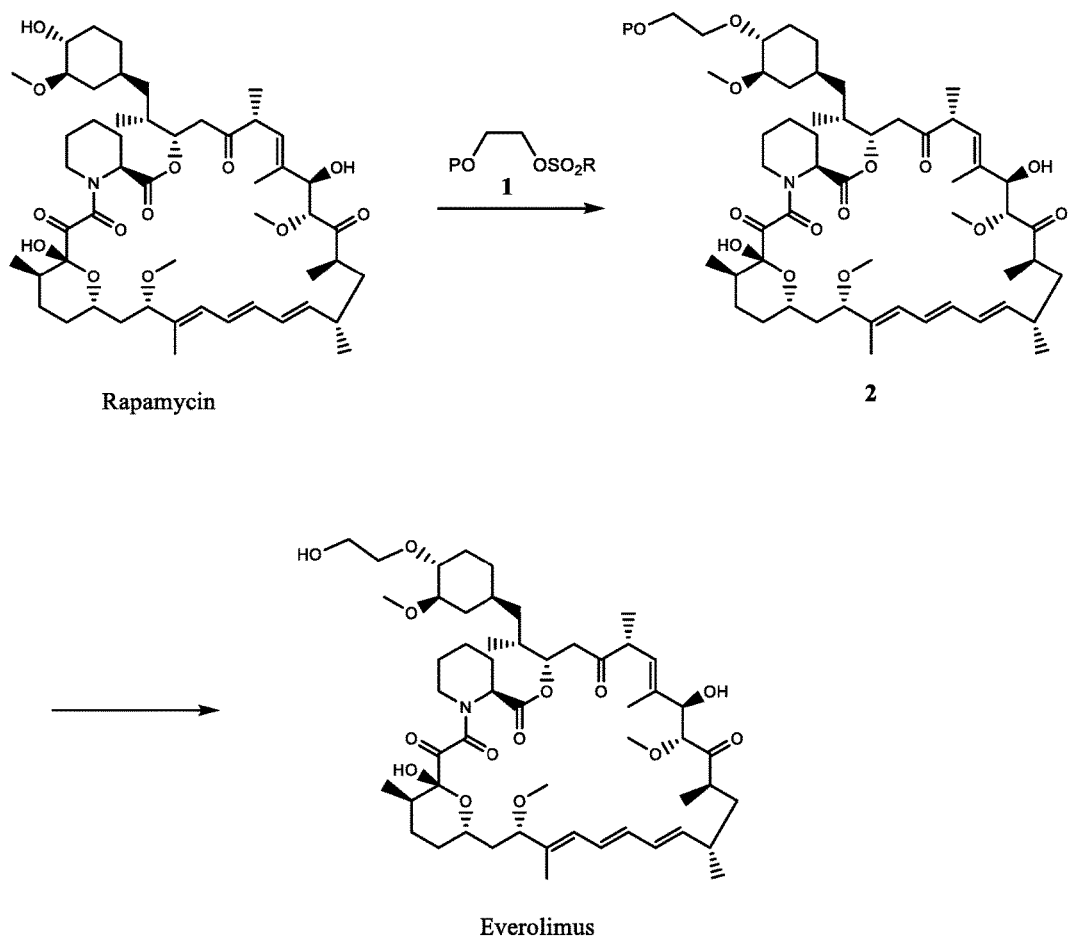
FIG. 2 illustrates a representative synthesis scheme for the production of everolimus being established in the art.
Figure 3:
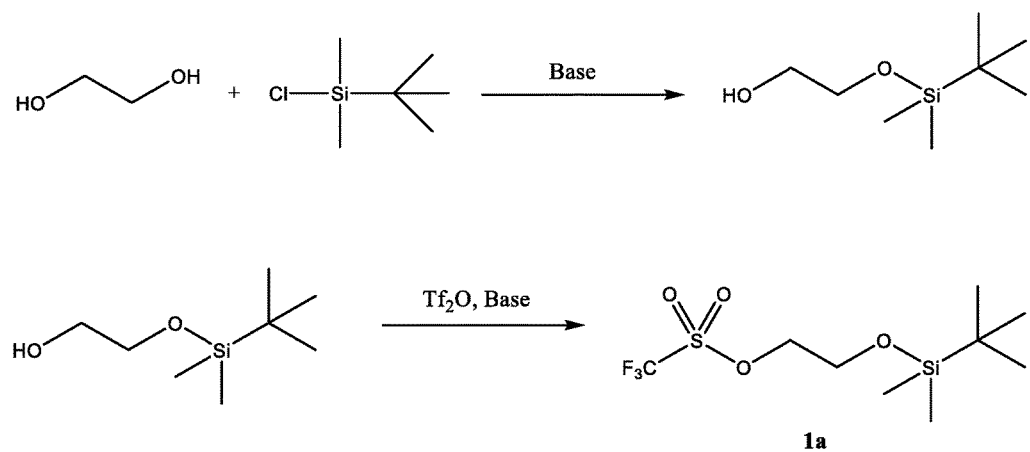
FIG. 3 illustrates a representative synthesis scheme for the preparation of 2-((t-butyl-dimethylsilyl)oxy)ethyl triflate being established in the art.

The present invention is based on the unexpected finding that by reacting ethylene oxide with t-butyldimethylsilyl trifluoromethanesulfonate in an organic solvent a highly pure 2-(t-butyldimethylsilyl)oxyethyl triflate is obtained that can be directly reacted with rapamycin in the presence of a molar excess of organic base to produce a silyl-protected rapamycin derivative (i.e., silyl-protected everolimus) in high yield and with a low portion of unwanted by-products. The silyl-protecting group can be removed under mild acidic conditions to obtain a pure rapamycin derivative (i.e., everolimus), thus providing for more cost-effective and less laborious overall synthesis scheme, concomitantly also resulting in improved yields of final product.

The present invention will be described in the following with respect to particular embodiments and with reference to certain drawings but the invention is to be understood as not limited thereto but only by the appended claims. The drawings described are only schematic and representative and are to be considered non-limiting.

Where the term "comprising" is used in the present description and claims, it does not exclude other elements or steps. For the purposes of the present invention, the term "consisting of" is considered to be a preferred embodiment of the term "comprising". If hereinafter a group is defined to comprise at least a certain number of embodiments, this is also to be understood to disclose a group, which preferably consists only of these embodiments.

Where an indefinite or definite article is used when referring to a singular noun e.g. "a", "an" or "the", this includes a plural of that noun unless specifically stated otherwise.

In case, numerical values are indicated in the context of the present invention the skilled person will understand that the technical effect of the feature in question is ensured within an interval of accuracy, which typically encompasses a deviation of the numerical value given of ±10%, and preferably of ±5%.

Furthermore, the terms first, second, third, (a), (b), (c), and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Further definitions of term will be given in the following in the context of which the terms are used. The following terms or definitions are provided solely to aid in the understanding of the invention. These definitions should not be construed to have a scope less than understood by a person of ordinary skill in the art.

In one aspect, the present invention relates to a method for the production of a rapamycin derivative of formula (I), comprising:

Formula (I)

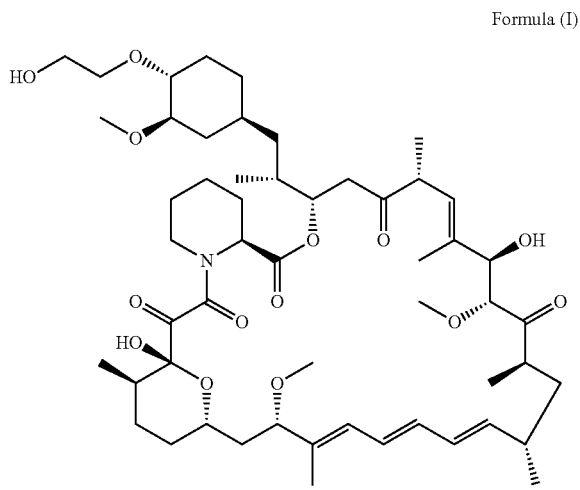 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

(a) preparing a 2-(tri-substituted silyl)oxyethyl triflate of formula 4 by reacting ethylene oxide and a tri-substituted silyl triflate of formula 3

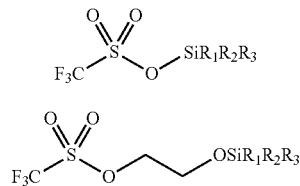

wherein $R_1$, $R_2$, and $R_3$ are independently selected from the group consisting of $C_1$-$C_{12}$ alkyl and $C_1$-$C_{12}$ aryl;

(b) reacting the 2-(tri-substituted silyl)oxyethyl triflate of formula 4 obtained in step (a) with rapamycin in the presence of a molar excess of organic base to obtain a protected rapamycin derivative of formula 5; and

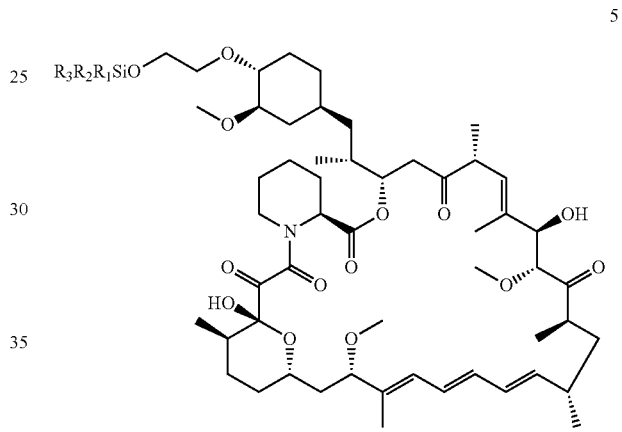

(c) deprotecting the protected rapamycin derivative of formula 5 to obtain the rapamycin derivative if formula (I).

Particularly, the rapamycin derivative of formula (I) being produced with the method of the present invention is everolimus. Analogously, in such setting the protected rapamycin derivative of formula 5 is protected everolimus.

Figure 4:
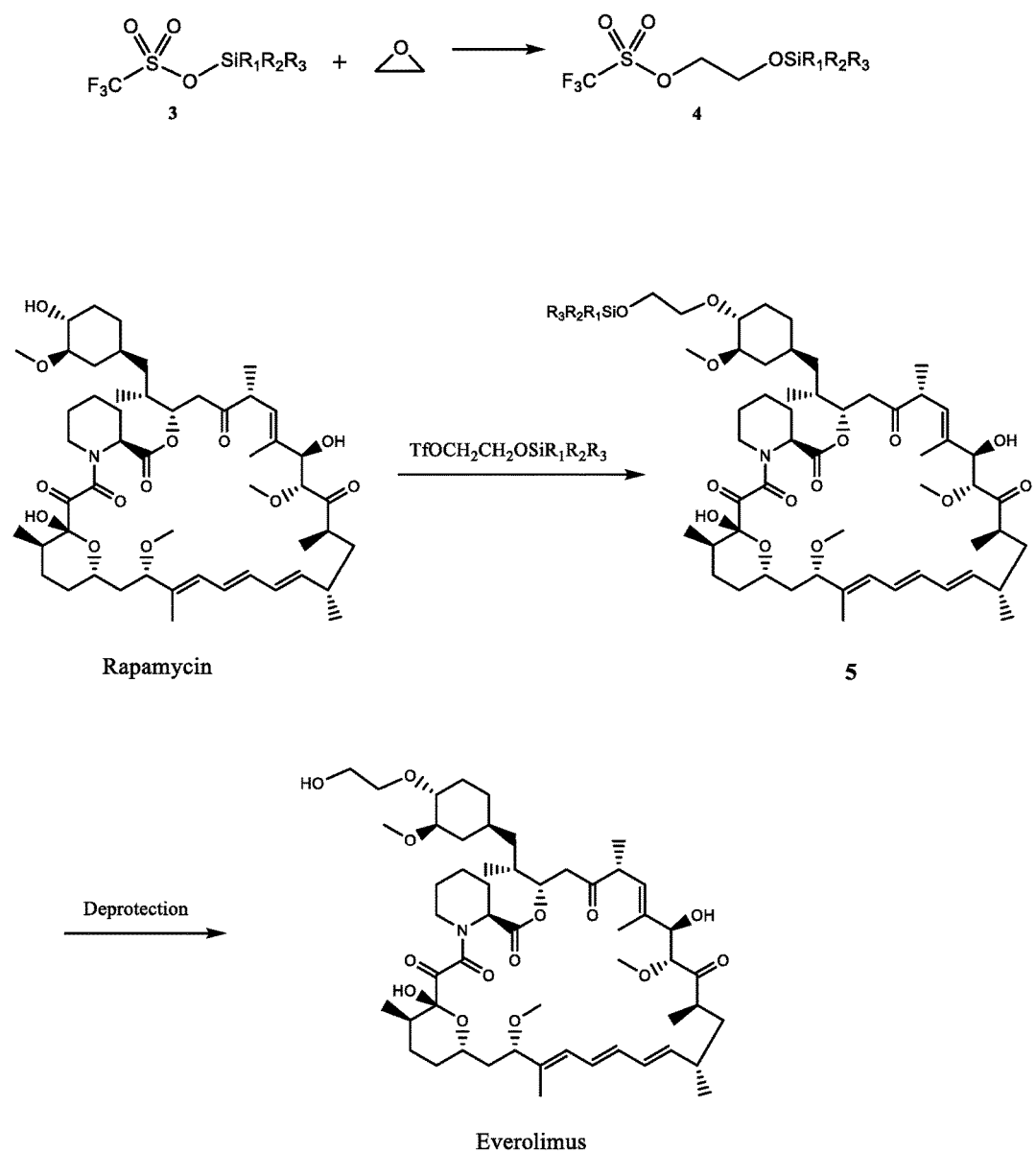
FIG. 4 illustrates a synthesis scheme for the production of everolimus according to the present invention.

The method according to the present invention is schematically illustrated in FIG. 4.

The reaction between ethylene oxide and the tri-substituted silyl triflate of formula 3 (i.e., method step (a)) may be performed at a reaction temperature in the range between −20° C. and 70° C. Typically, the reaction is performed at a temperature in the range between 0° C. and 60° C. or in the range between 10° C. and 50° C. In preferred embodiments, the reaction is performed at a temperature in the range between 15° C. and 45° C. or in the range between 20° C. and 40° C. The reaction may be performed at a temperature of 15° C., 20° C., 25° C., 30° C., 35° C., 40° C., and 45° C.

The reaction may be performed in an organic solvent, and particularly in an inert organic solvent, that is, a solvent that does not react with the reactants. In specific embodiments, the organic solvent is selected from the group consisting of toluene, acetonitrile, dichloromethane, heptane, pentane, hexane, benzene, xylene, and mixtures thereof. Accordingly, the organic solvent employed herein may also represent a mixture of two or more individual solvents, such as toluene and dichloromethane. Particularly preferably, the organic solvent employed is toluene.

Typically, the ethylene oxide may be used in this reaction in an amount ranging from 1.0 to 1.6 molar equivalents of the amount of tri-substituted silyl triflate of formula 3 employed. Preferably, the ethylene oxide is used in an amount of 1.0-1.3 molar equivalents or in an amount of 1.1-1.2 equivalents of the amount of tri-substituted silyl triflate of formula 3 employed.

The substituents $R_1$, $R_2$, and $R_3$ of the tri-substituted silyl triflate of formula 3 may independently represent any $C_1$-$C_{12}$ alkyl group or $C_1$-$C_{12}$ aryl group, thus including straight, branched or cyclic substituents with one to twelve carbon atoms. The terms "alkyl" and "aryl" are used herein in accordance with their standard meaning in the art. For example, straight alkyl groups in accordance with the present invention include methyl, ethyl, propyl, butyl, pentyl, hexyl, heptyl, octyl, nonyl, decyl, undecyl, and dodecyl. Branched alkyl groups include inter alia iso-butyl, sec-butyl, tert-butyl (t-butyl), iso-propyl, t-propyl, iso-hexyl, t-hexyl, and so forth. Exemplary aryl groups include phenyl and naphthyl. The substituents may also include heteroatoms or may be substituted, for example, with a hydroxyl or an amine group.

In particular embodiments, $R_1$, $R_2$, and $R_3$ are independently selected from the group consisting of $C_1$-$C_6$ alkyl and $C_6$-$C_{12}$ aryl. In a preferred embodiment, $R_1$, $R_2$, and $R_3$ each are isopropyl. In another preferred embodiment, $R_1$ and $R_2$ each are methyl, and R3 is t-butyl. In yet another preferred embodiment, $R_1$ and $R_2$ each are phenyl, and R3 is t-butyl. In yet another preferred embodiment, $R_1$ and $R_2$ each are methyl, and R3 is t-hexyl.

In contrast to established methods starting from ethylene glycol, the method for the preparation of the 2-(tri-substituted silyl)oxyethyl triflate of formula 4 according to the present invention represents a one-step process resulting in high yield as well as high purity of the product which, in turn, does not require any further purification before subjecting it to subsequent reaction steps. In addition, no special equipment for performing extensive cooling or distillation is required, thus making the method of the present invention readily applicable for industrial-scale manufacturing.

In particular embodiments, the 2-(tri-substituted silyl) oxyethyl triflate of formula 4 obtained in step (a) is thus used without further purification.

The synthesis of protected everolimus (i.e., method steps (a) and (b)) may be performed as a "one-pot" procedure by adding rapamycin in the presence of a molar excess of organic base to ethylene oxide and a tri-substituted silyl triflate of formula 3 and heating the resulting reaction mixture. In such setting, the 2-(tri-substituted silyl)oxyethyl triflate of formula 4 is an intermediate reaction product which is directly used for the condensation with rapamycin.

Method step (b) may be performed at a reaction temperature in the range between 20° C. and 70° C. Typically, the reaction is performed at a temperature in the range between 30° C. and 60° C. In preferred embodiments, the reaction is performed at a temperature in the range between 40° C. and 55° C., and particularly preferably in the range between 48° C. and 50° C. The reaction may be performed at a temperature of 40° C., 42° C., 44° C., 46° C., 48° C., 50° C., 52° C., and 55° C.

The reaction may be performed in an organic solvent, and particularly in an aprotic organic solvent, that is, a solvent that cannot donate hydrogen. In specific embodiments, the organic solvent is selected from the group consisting of toluene, acetonitrile, dichloromethane, heptane, pentane, hexane, benzene, xylene, dimethoxyhexane, and mixtures thereof. Accordingly, the organic solvent employed herein may also represent a mixture of two or more individual solvents, such as toluene and dimethoxyethane. Particularly preferably, the organic solvent employed is a mixture of 85-95% (v/v) toluene and 5-15% (v/v) dimethoxyethane.

Typically, the the 2-(tri-substituted silyl)oxyethyl triflate of formula 4 may be used in this reaction in an amount ranging from 1 to 30 molar equivalents or 2 to 20 molar equivalents of the amount of rapamycin employed. Preferably, the 2-(tri-substituted silyl)oxyethyl triflate of formula 4 is used in an amount of 4 to 12 molar equivalents or 5 to 8 molar equivalents of the amount of rapamycin, with 6 molar equivalents being particularly preferred.

Method step (b) is performed with a molar excess of organic base in order to neutralize the triflic acid formed during the reaction. Concomitantly, it has been found that the addition of organic base reduces undesired side reactions, and thus aids in both obtaining a product with improved purity and simplifying the overall synthesis scheme. Examples of suitable organic bases include inter alia N,N-diisopropylethylamine, 2,6-lutidine, 2,6-di-tert-butylpyridine, and mixtures thereof. Particularly preferably, the organic base is N,N-diisopropylethylamine.

In other particular embodiments, the protected everolimus of formula 5 obtained in step (b) is used without further purification.

The deprotection step (i.e., method step (c)) may be performed using appropriate reaction conditions, particularly mild acidic conditions, known in the art in order to remove the silyl protection group from the protected everolismus of formula 5.

In preferred embodiments, deprotection is accomplished by reacting the protected everolimus of formula 5 with an agent selected from the group consisting of hydrochloric acid, acetic acid, tetra-n-butylammonium fluoride, and pyridine hydrofluoride.

In other particular embodiments, the method further comprises purifying the everolimus obtained in step (c), for example by affinity chromatography and/or by subsequent crystallization. Various such purification methods are well established in the art.

The invention is further described by the figures and the following examples, which are solely for the purpose of illustrating specific embodiments of this invention, and are not to be construed as limiting the claimed subject matter in any way.

EXAMPLES

Example 1

Synthesis of 40-O-[2-(t-butyldimethylsilyl)oxy] ethyl-rapamycin

A mixture of 7.9 ml of 1M ethylene oxide solution in toluene and 1.01 g of N,N-diisopropylethylamine was added under stirring to 1.72 g of t-butyldimethylsilyl trifluoromethanesulfonate. The resulting mixture was stirred for further 40 min at 20° C. Then, 0.66 ml of 1,2-dimethoxyethane and 1.82 g of N,N-diisopropylethylamine trifluoromethanesulfonate were added. The resulting mixture was stirred at 20° C. until complete dissolution, before 1.0 g of rapamycin was added. The reaction mixture was purged with nitrogen for 10 min, heated to 48-50° C. and stirred at this temperature for 18 h. Subsequently, the reaction mixture was cooled to 20° C., and 0.2 ml of pyridine and 16 ml of heptane were added. The resulting mixture was stirred for 10 minutes. The precipitate formed was obtained by filtration and washed with a mixture of 4.0 ml of toluene and 9.4 ml of heptane. Then, 1 ml of 0.2% solution of 2,6-di-t-butyl-4-methylphenol in heptane was added to the filtrate and the resulting crude 40-O-[2-(t-butyldimethylsilyl)oxy]ethyl-rapamycin solution was subjected to the deprotection step. HPLC analysis of the obtained 40-O-[2-(t-butyldimethylsilyl)oxy]ethyl-rapamycin solution showed an overall yield of 76% (895 mg).

Example 2

Synthesis of 40-O-(2-hydroxy)ethyl-rapamycin (i.e. everolimus)

The crude 40-O-[2-(t-butyldimethylsilyl)oxy]ethyl-rapamycin solution of Example 1 was evaporated to dryness under reduced pressure at 25-30° C. Subsequently, 66 ml of heptane were added to the residue, and the resulting mixture was evaporated to a volume of 40 ml. Then, 48 ml of a (80:20) (v/v) mixture of acetonitrile/water (pH=1.7, adjusted with 75% ortho-phosphoric acid) were added, and the pH of the resulting mixture was adjusted to 1.8 with 1N HCl solution. The resulted mixture was stirred for 1 hour at room temperature, and the lower layer containing everolimus was separated. The overall yield of everolimus as determined by HPLC using an external standard was 68% (711 mg).

Example 3

Synthesis of 40-O-[2-(thisopropylsilyl)oxy]ethyl-rapamycin

A mixture of 7.9 ml of 1M ethylene oxide solution in toluene and 1.01 g of N,N-diisopropylethylamine was added under stirring to 1.99 g of triisopropylsilyl trifluoromethanesulfonate. The resulting mixture was stirred for further 1 hour at 40° C. Then, 0.66 ml of 1,2-dimethoxyethane and 1.82 g of N,N-diisopropylethylamine trifluoromethanesulfonate were added. The resulting mixture was stirred at 20° C. until complete dissolution, before 1.0 g of rapamycin was added. The reaction mixture was purged with nitrogen for 10 min, heated to 48-50° C. and stirred at this temperature for 18 h. Subsequently, the reaction mixture was cooled to 20° C., and 0.2 ml of pyridine and 16 ml of heptane were added. The resulting mixture was stirred for 10 minutes. The precipitate formed was obtained by filtration and washed with a mixture of 4.0 ml of toluene and 9.4 ml of heptane. Then, 1 ml of 0.2% solution of 2,6-di-t-butyl-4-methylphenol in heptane was added to the filtrate and the resulting crude 40-O-[2-(tri-isopropylsilyl)oxy]ethyl-rapamycin solution was subjected to deprotection. HPLC analysis of the obtained 40-O-[2-(triisopropylsilyl)oxy]ethyl-rapamycin solution showed an overall yield of 71% (864 mg).

Example 4

Synthesis of 40-O-(2-hydroxy)ethyl-rapamycin (i.e. everolimus)

The crude 40-O-[2-(triisopropylsilyl)oxy]ethyl-rapamycin solution of Example 3 was evaporated to dryness under reduced pressure at 25-30° C. Subsequently, 66 ml of heptane were added to the residue, and the resulting mixture was evaporated to a volume of 40 ml. Then, 48 ml of a (80:20) (v/v) mixture of acetonitrile/water (pH=1.7, adjusted with 75% ortho-phosphoric acid) were added, and the pH of the resulting mixture was adjusted to 1.8 with 1N HCl solution. The resulted mixture was stirred 1 day at room temperature, and the lower layer containing everolimus was separated. The overall yield of everolimus as determined by HPLC using an external standard was 64% (668 mg).

Example 5

Synthesis of 40-O-[2-(t-butyldiphenylsilyl)oxy]ethyl-rapamycin

A mixture of 7.9 ml of 1M ethylene oxide solution in toluene and 1.01 g of N,N-diisopropylethylamine was added under stirring to 2.53 g of t-butyldiphenylsilyl trifluoromethanesulfonate. The resulting mixture was stirred for further 1 hour at 40° C. Then, 0.66 ml of 1,2-dimethoxyethane and 1.82 g of N,N-diisopropylethylamine trifluoromethanesulfonate were added. The resulting mixture was stirred at 20° C. until complete dissolution, before 1.0 g of rapamycin was added. The reaction mixture was purged with nitrogen for 10 min, heated to 48-50° C. and stirred at this temperature for 18 h. Subsequently, the reaction mixture was cooled to 20° C., and 0.2 ml of pyridine and 16 ml of heptane were added. The resulting mixture was stirred for 10 minutes. The precipitate formed was obtained by filtration and washed with a mixture of 8.0 ml of toluene and 8.0 ml of heptane. Then, 1 ml of 0.2% solution of 2,6-di-t-butyl-4-methylphenol in heptane was added to the filtrate and the resulting crude 40-O-[2-(t-butyldiphenylsilyl)oxy]ethyl-rapamycin solution was subjected to the deprotection step. HPLC analysis of the obtained 40-O-[2-(t-butyldiphenylsilyl)oxy]ethyl-rapamycin solution showed an overall yield of 71% (932 mg).

The present invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modifications and variations of the inventions embodied therein may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The invention claimed is:

1. Method for the production of a rapamycin derivative of formula (I), comprising:

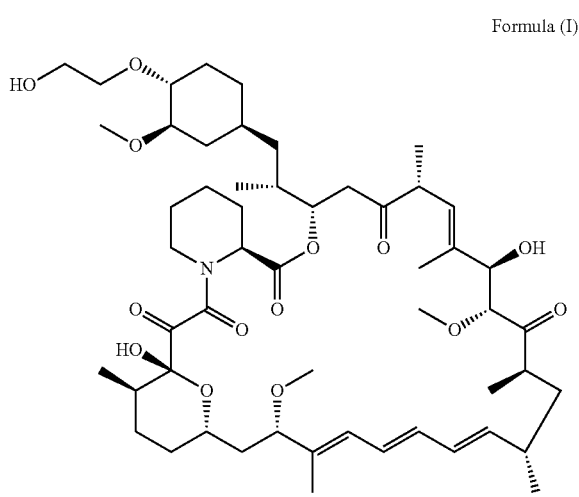 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OCCO)[C@H](OC)C2)CC(=O)[C@H](C)/C=C(\C)[C@@H](O)[C@@H](OC)C(=O)[C@H](C)C[C@H](C)/C=C/C=C/C=C/1C]

Formula (I)

(a) preparing a 2-(tri-substituted silyl)oxyethyl triflate of formula 4 by reacting ethylene oxide and a tri-substituted silyl triflate of formula 3

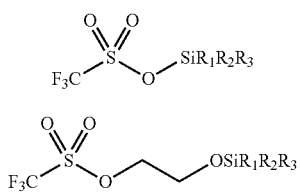

wherein $R_1$, $R_2$, and $R_3$ are independently selected from the group consisting of $C_1$-$C_{12}$ alkyl and $C_1$-$C_{12}$ aryl;

(b) reacting the 2-(tri-substituted silyl)oxyethyl triflate of formula 4 obtained in step (a) with rapamycin in the presence of a molar excess of organic base to obtain a protected rapamycin derivative of formula 5; and

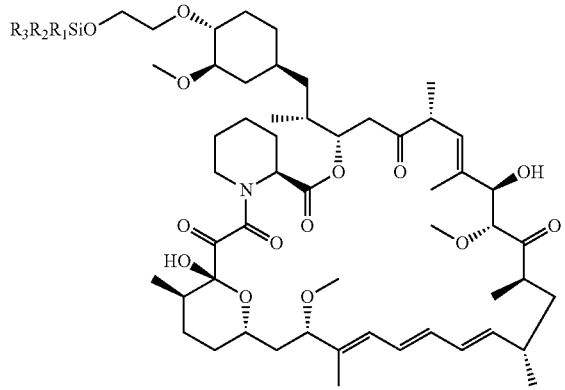

(c) deprotecting the protected rapamycin derivative of formula 5 to obtain the rapamycin derivative if formula (I).

2. The method of claim 1, wherein $R_1$, $R_2$, and $R_3$ are independently selected from the group consisting of $C_1$-$C_6$ alkyl and $C_6$-$C_{12}$ aryl.

3. The method of claim 1, wherein $R_1$, $R_2$, and $R_3$ each are isopropyl; or $R_1$ and $R_2$ each are methyl and $R_3$ is t-butyl; or $R_1$ and $R_2$ each are phenyl and $R_3$ is t-butyl; or $R_1$ and $R_2$ each are methyl and $R_3$ is t-hexyl.

4. The method of claim 1, wherein step (a) is performed at a reaction temperature of 15° C.-45° C. in an organic solvent.

5. The method of claim 4, wherein the organic solvent is toluene.

6. The method of claim 1, wherein the ethylene oxide is used in an amount of 1.1-1.2 molar equivalents of the amount of tri-substituted silyl triflate of formula 3.

7. The method of claim 1, wherein the 2-(tri-substituted silyl)oxyethyl triflate of formula 4 obtained in step (a) is used without further purification.

8. The method of claim 1, wherein step (b) is performed at a reaction temperature of 40° C.-55° C. in an organic solvent.

9. The method of claim 8, wherein the organic solvent is a mixture of 85-95% (v/v) toluene and 5-15% (v/v) dimethoxyethane.

10. The method of claim 1, wherein the 2-(tri-substituted silyl)oxyethyl triflate of formula 4 is used in an amount of 4-12 molar equivalents of the amount of rapamycin.

11. The method of claim 1, wherein the organic base in step (b) is N,N-diisopropylethylamine.

12. The method of claim 1, wherein the protected rapamycin derivative of formula 5 obtained in step (b) is used without further purification.

13. The method of claim 1, wherein deprotection is accomplished by reacting the protected rapamycin derivative of formula 5 with an agent selected from the group consisting of hydrochloric acid, acetic acid, tetra-n-butylammonium fluoride, and pyridine hydrofluoride.

14. The method of claim 1, further comprising purifying the rapamycin derivative of formula (I) obtained in step (c).

* * * * *

UNITED STATES PATENT AND TRADEMARK OFFICE
CERTIFICATE OF CORRECTION

PATENT NO.        : 10,308,665 B2
APPLICATION NO.   : 15/737861
DATED             : June 4, 2019
INVENTOR(S)       : Oleksandr Zabudkin et al.

It is certified that error appears in the above-identified patent and that said Letters Patent is hereby corrected as shown below:

In the Claims

At Column 12, Claim number 1, Line number 21, replace "if" with -- of --.

Signed and Sealed this
Thirtieth Day of July, 2019

Andrei Iancu
*Director of the United States Patent and Trademark Office*